United States Patent [19]

Olah

[11] 4,201,730

[45] May 6, 1980

[54] HYDROCARBON CONVERSIONS USING SOLID SUPERACID CATALYSTS BASED ON FLUORINATED GRAPHITE

[75] Inventor: George A. Olah, Shaker Heights, Ohio

[73] Assignee: Produits Chimiques Ugine Kuhlmann, Paris, France

[21] Appl. No.: 878,336

[22] Filed: Feb. 16, 1978

Related U.S. Application Data

[62] Division of Ser. No. 807,014, Jun. 16, 1977, Pat. No. 4,116,880.

[51] Int. Cl.[2] .......... C07C 2/58

[52] U.S. Cl. .......... 585/730; 585/749; 585/752

[58] Field of Search .......... 260/683.68, 683.2

[56] References Cited

U.S. PATENT DOCUMENTS

| | | | |
|---|---|---|---|
| 3,925,495 | 12/1975 | Rodewald | 260/683.68 |
| 3,948,761 | 4/1976 | Siskin | 260/683.68 |
| 3,962,133 | 6/1976 | Rodewald | 260/683.68 |
| 3,984,352 | 10/1976 | Rodewald | 260/683.68 |

OTHER PUBLICATIONS

F. Albert Cotton, Adv. Inorg. Chem., Interscience, N.Y. 1972, pp. 168-182.

George A. Olah et al., J. Org. Chem. 42, 1977, pp. 4187-4191.

Croft, Research, Science and Its Applications in Industry, vol. 10, London, Buffersworth Sci. Pub. Jan. 1957, pp. 23-28.

A. R. Ubbelohde et al. Graphite and Its Crystal Compounds, Oxford, Clarendon, 1960, pp. 123-127.

Gerhart R. Hennig, Interstitial Compounds of Graphite, pp. 126-205.

Jean M. Lalancette et al., J. Chem. Soc. Chem. Comm., 1973, p. 815.

G. R. Hennig et al., Third Biennial Carbon Conf., pp. 349-354.

G. R. Hennig et al., Proceedings of Conferences of Carbon, pp. 103-112.

Von Heinrich Thieles, Zeit. fur. Anorgan und Alkemenie Chemie., Band 207, 1932, pp. 340-352.

W. Rudorff, Kristallstraktur der Saureverbindungen des Graphite, 1939, ppp. 42-68.

*Primary Examiner*—Veronica O'Keefe
*Attorney, Agent, or Firm*—Pennie & Edmonds

[57] ABSTRACT

A process and a catalyst composition to effect hydrocarbon transformations comprising contacting a hydrocarbon charge with a catalyst comprising a fluorinated graphite having a fluorine to carbon atomic ratio of from about 0.1 to 1 and having bonded thereto from about 5 to 50 percent by weight of the total weight of the catalyst of at least one Lewis acid compound selected from halides of the elements of Group IIA, IIIA, IVB, V or VIB of the Periodic Table. In addition, the catalysts may also have bonded thereto a minor portion of a Bronsted acid and/or a metal of Group IVB or VIII of the Periodic Table.

9 Claims, No Drawings

HYDROCARBON CONVERSIONS USING SOLID SUPERACID CATALYSTS BASED ON FLUORINATED GRAPHITE

This is a division, of application Ser. No. 807,014, filed June 16, 1977, now U.S. Pat. No. 4,116,880.

BACKGROUND OF THE INVENTION

For nearly a century Friedel-Crafts reactions were carried out in solution using $AlCl_3$ and related Lewis acid halide type catalysts. These reactions, some of which gained very significant industrial application, such as the ethylation of benzene, and the isomerization of hydrocarbons, are all well recognized to involve the formation of highly colored complex layers (so called "red oils"). These complexes are now understood to contain significant concentrations of carbocationic tetrachloroaluminate salts and tie-up large amounts of the catalyst in its catalystically inactive coordinated anion form. Further, decomposition of the complex layers necessitates additional steps and generally results in the loss of the catalyst.

The realization of the nature of the Friedel-Crafts reactions and their catalyst resulted in an understanding of the generalized acid catalyzed characteristics of these reactions, and allowed the use of a large variety of not only Lewis, but of Bronsted type catalyst systems. The use of supported solid acid catalysts, allowing catalytic heterogenous reactions, was, until very recently, of limited scope. They utilized only in specific instances, such as in the preparation of cumene via propylation of benzene with propylene, using catalysts of the supported solid phosphoric acid type. Similar reaction conditions for the preparation of ethylbenzene from benzene and ethylene were found less satisfactory. Ethylation was observed to take place only at higher temperatures, and even more significantly, the transethylation of benzene with di- or polyethylbenzenes, inevitably formed in the reactions, is not satisfactorily realized under heterogenous catalytic conditions.

Friedel-Crafts isomerization of hydrocarbons, such as of alkanes to highly branched isomeric mixtures of the isomerization of dialkylbenzenes, such as xylenes, was also until now predominantly carried out with liquid Friedel-Crafts catalyst systems such as $AlBr_3$, $AlCl_3$, $HFBF_3$ etc.

Nonbonded electron-pair containing systems such as aldehydes, ketoes, and the like, when formed in Friedel-Crafts reactions, coordinate equilmolar amounts of $AlCl_3$, or related catalysts and thus generally necessitate the use of molar excess of "catalyst", as well as decomposition of stable catalyst-product complexes. These and related conditions limit the industrial and practical use of Friedel-Crafts reactions compared with other catalytic systems, such as metal and organometallic catalyzed transformation reactions, isomerization, and the like.

It is on this basis, consequently, that there is substantial practical significance in this invention to modify the usual Friedel-Crafts type reactions in a way which can be described on the basic principle to bind the catalyst to a suitable solid surface or carrier which would then allow the use of these systems as effective solid acid catalysts.

DESCRIPTION OF THE PRIOR ART

Magic Acid type superacid catalysts, such as $FSO_3H$-$Sbf_5$ or fluoroantimonic acid HF-$SbF_5$, have an estimated acidity on the logarithmic Hammett acidity scale of about $-25$ (as compared with $-11$ for 100% sulfuric acid, or $-10$ for 100% HF) are thus many times stronger than conventional strong mineral acids.

The ability of antimony pentafluoride, tantalum pentafluoride, niobium pentafluoride and the like Lewis acid fluorides to catalyze hydrocarbon transformation reactions is due to the formation with any proton source (inevitably present in the feed hydrocarbons or from atmospheric moisture) of their conjugate superacids. The solution chemistry of superacids was well documented in recent years in our work. It was based on this background that it was attempted to attach these superacid systems to suitable solid supports. Difficulties in achieving this goal are, however, significant. For example, $BF_3$ based systems such as the HF-$BF_3$, cannot be absorbed into solid supports because of the great ease with which $BF_3$ is desorbed from these solid supports. As $SbF_5$, $TaF_5$, $NbF_5$ have much lower vapor pressures and increased ability for fluorine-bridging, they are much more adaptable to be attached to solid supports. Due to the extreme chemical reactivity of $SbF_5$, it was found that it can be attached only satisfactorily to fluorinated carriers, such as fluorinated-alumina.

$SbF_5$-$FSO_3H$ (magic acids) on fluorinated-alumina, at 70°, isomerizes straight chain alkenes such as n-heptane, or n-hexane. Similar systems are also effective as alkylation catalysts of alkanes with alkenes.

The fluorinated-alumina surfaces can also be prepared in situ when alumina or other chalcides (alumina-tungsta, alumina-silica, alumina-wolframa, or alumina-titana) are treated with excess $SbF_5$ at temperatures between 300° and 450° C. During the catalyst preparation process active hydroxyl sites of the chalcides are fluorinated, and the thus formed fluorinated surface then complexes $SbF_5$. These catalysts are effective for isomerization and alkylation reactions, but still show limited adherence of the catalyst to the surface.

We have also found that $SbF_5$, $NbF_5$ and $TaF_5$ based superacids can be deposited on inert polyfluoroinated polymer supports (Teflon, Kel-F and the like) or on fluorinated polycarbon (coke). Adherence to these surfaces, however, is again limited.

It has been known for nearly a century that layer compounds, such as graphite, under suitable conditions possess a significant ability to form intercalated systems with a large variety of chemicals, including Friedel-Crafts type Lewis acid halides, as well as their conjugate, protonic acids, and the like. For example, $AlCl_3$ can be readily intercalated into graphite under suitable conditions. Thus intercalated graphite-$AlCl_3$ (or related ferric chloride, gallium chloride, or the like) systems can be readily prepared. The application of these systems as catalysts for hydrocarbon transformations is suprisingly limited. Only recently did a report appear on the use of intercalated graphite $AlCl_3$ as a Friedel-Crafts catalyst, however, using it mainly in liquid phase systems as a dispersed catalyst (J. M. Lalancette, M. J. Fournier-Breault and R. Thiffault, Can. J. Chem. 52, 589 1974). Heterogeneous vapor phase reactions over intercalated Friedel-Crafts and superacidic catalysts were first reported by G. A. Olah (lecture First North American Chemical Congress, Mexico City, December 1975 "Hydrocarbon Transformation Reactions Over Solid Superacids and Intercalated Friedel-Crafts Catalysts" Abstr. Papers PHSC 153). The ethylation of benzene with ethylene or the related transethylation of benzene with dialkylbenzene were, inter alia, studied using 16% and 28% inercalated $AlCl_3$ catalyst at representative temperatures of 125° and 160° respectively. It was found that, indeed, benzene is readily ethylated with ethylene with good yield (62% and 60.4% respectively). A recent U.S. Pat. to Mobil Oil, No. 3,925,495 (issued Dec. 9, 1975) also disclosed the use of intercalated halides in graphite for heterogeneous reactions.

Our ESCA spectroscopic studies, however, showed that the reactions with graphite intercalates take place only with the catalytic halide on the exposed edges of the surface, and not in the deeper intercalated graphite layers. This is shown by study of deactivated catalyst, which according to elemental analysis still contain significant (up to 35%) of aluminum halide in the deeper layers, but became deactivated (as shown by surface studies using ESCA spectroscopy) because the catalytic halide is not chemically bonded to the surface, and thus is readily hydrolyzed by inevitable moisture or other impurities in the feed, or is extracted by the organic reagents. Similar observations were made with graphite-antimony pentafluoride intercalate.

ESCA studies comparing fresh and used $AlCl_3$ and $SbF_5$ graphite catalysts clearly indicated a significant decrease of active catalyst on the exposed upper surfaces of the catalysts. Overall $AlCl_3$ and $SbF_5$ analysis at the same time showed that the deactivated catalyst still contained at least 85% of its original halide content.

Graphite-$AlCl_3$, graphite-$AlBr_3$, and graphite-$SbF_5$ intercalates were also studied in their ability to isomerize alkanes, such as, for example n-heptane. Not unlike in solution chemistry $AlBr_3$ proved to be a better catalyst than $AlCl_3$. Significantly, the aluminum halide catalyst and particularly the $SbF_5$-graphite catalyst, also promote C-C bond cleavage reactions, thus producing significant amounts of $C_4$, and $C_3$ cleavage products. These catalysts thus are also adaptable as cracking catalysts.

The limitations of graphite intercalated Friedel-Crafts or superacidic catalysts are obvious from the foregoings. Catalysts intercalated into the deeper layers have no activity in the reactions. Clearly, the interspacial distances are not sufficient to allow reagent penetration, resulting in basically surface catalyzed reactions, or taking place only in the upper and more exposed graphite layers. In these exposed or more easily available surfaces, the catalyst present is not bound by any chemical forces, and, therefore, is readily deactivated or extracted by the organic reactants and any impurity, first of all moisture, which are inevitable in the systems.

SUMMARY OF THE INVENTION

The present invention relates to a catalyst comprising a fluorinated graphite having a fluorine to carbon atomic ratio of from about 0.1 to 1 and having bonded thereto at least one Lewis acid compound selected from the halides of the elements of Groups IIA, IIIA, IVB, V or VIB of the Periodic Table, and to such which also have a minor amount of a Bronsted Acid and/or a metal selected from the metals of Groups VIB, or VIII of the Periodic Table bonded to the fluorinated support. The invention includes a process for catalytic transformation of hydrocarbons.

The present catalyst system comprising solid Lewis acid or Lewis-Bronsted acid bonded to a fluorinated graphite support has catalytic activity of extended duration in comparison to previously known supported catalysts.

DETAILED DESCRIPTION OF THE INVENTION

The graphite supports utilized in the present catalyst system are fluorinated graphites having a fluorine to carbon atomic ratio of from about 0.1 to 1. The best results are obtained with a fluorinated graphite in which the atomic ratio of the fluorine to carbon is between 0.1 to 0.5.

The duration of the treatment and the quantity of halogenating agent to be used are to be determined in accordance with conventional techniques so as to produce a support having a desired fluorine to carbon atomic ratio.

The present catalytic process for hydrocarbon transformation requires the presence of a heterogeneous catalyst comprising a fluorinated graphite which has bound to it a Lewis acid of the formula $MX_n$ wherein M is a metal selected from the metals of the Group IIA, IIIA, IVB, V, VIB of the Periodic Table; X is a halogen such as chlorine, bromine or fluorine and the like and n is an integer of from 2 to 6 and is compatible with the valance of the metal M. Lewis acid halides have been found to readily bond to the fluorographite suport to form a catalyst having an activity of long duration. The Lewis acid halides are well known to those skilled in the art and are represented by compounds of antimony pentafluoride, niobium pentafluoride, tentalum pentafluoride, titanium tetrafluoride, bismuth pentafluoride, molybdenum hexafluoride, arsenic pentafluoride, phosphorus pentafluoride, aluminum chloride, terric chloride, beryllium chloride and the like. In addition to the fluorides, the chlorides, bromides, or iodides may be employed. The amount of Lewis acid bound to the fluorinated graphite support is generally from between about 5 and 50 percent by weight of the total catalyst composition.

The bonding of the Lewis acid catalysts to the fluorinated graphite is readily effected by heating a mixture of fluorinated graphite and a Lewis acid halide at a temperature of between about 50° and 200° C. and preferably at a temperature of from about 80° to 150° C. for a period of from about 30 minutes to 24 hours.

The Lewis acid halide supported catalysts of the present invention can, in addition, contain a minor amount of a Bronsted acid such as a hydrogen fluoride, fluorosufuric acid or trifluoromethane sulfuric acid. The Bronsted acid is also chemically bound to the fluorinated graphite and is used in amounts such that the Bronsted acid is present in amounts of between about 1 and 50 percent by weight based on the weight of the Lewis acid.

Further, the catalysts of the present invention may also contain a metal of the metals of Groups VIB or VIII of the Periodic Table bonded to the fluorographite in amounts of from about 0.1 to 5 percent by weight based on the weight of the Lewis acid. Representative metals include nickel, cobalt, iron, chromium, molybdenum, tungsten, and the like. Group VIII metals are preferred, especially the metals of platinum, palladium, rhodium, and rhenium.

When a metal of the metals of Groups IVB or VIII is a desired addition to the catalysts, it can be introduced into the fluorinated graphite by treating a compound of the appropriate metal with the fluorinated graphite at a temperature generally between 50° and 200° C. for a period between 1 and 24 hours. The metal salts are subsequently reduced to the metal by the treatment with hydrogen. Normally, the thus treated fluorinated graphite is then further treated with the desired Lewis acid halide to provide a bifunctional acid catalyst. In a similar manner, when a Bronsted acid is additionally desired as a component of the catalyst, the catalyst is formed by first treating the fluorinated graphite support with a Lewis acid as discussed hereinabove and then further treating the fluorinated graphite support with the desired Brontsted acid at a temperature between about −20° and +150° C. for a period between about 30 minutes and 2 hours.

A wide variety of hydrocarbon transformer reactions are readily catalyzed with the catalysts of the instant invention as described hereinabove. These reactions include alkylation, isomerization, polymerization, oligo- and co-condensation, disproportionation, cracking, de- and transalkylations and related processes. These processes are effected by contacting a charge of a hydrocarbon, or hydrocarbon mixture with the above described catalysts under the conventional conditions of the desired hydrocarbon conversion. The catalyst to hydrocarbon ratio is normally from about 1:5 to about 1:20. Contacting of the catalyst with the hydrocarbon charge is facilitated by using such conventional systems as fixed bed systems, moving bed systems, fluidized bed systems, continuous or batch-type operations. The hydrocarbon conversions utilizing the presently described catalysts can be carried out either in the vapor phase, in the liquid phase, or as mixed phase operations. Conversions can be also carried out in the presence of hydrogen, or naphthenic hydrocarbons as moderators which tend to decrease any concurrent cracking reactions. Operation in the presence of hydrogen and related hydrocarbon moderators are particularly advantageous for isomerizations in preserving catalyst life. In these instances, Lewis acid halides with high redox potentials are preferred, such as tantalum pentafluoride, niobium pentafluroide and the like, over more easily reducible halides, such as antimony pentafluoride.

Isomerization of isomerizable $C_4$ to $C_{30}$ hydrocarbons such as paraffins, naphthenes or alkyl-aromatic hydrocarbons may be effectively carried out utilizing the catalysts of this invention. Isomerization of straight-chain or slightly branched-chain paraffins containing 4 or more carbon atoms in their molecules, such as n-butane, n-pentane, n-hexane, n-heptane, n-octane, and the like, may be readily effected. Likewise, cycloparaffins containing at least 5 carbon atoms in the ring, such as alkyl cyclopentanes and cyclohexanes may be effectively isomerized. These isomerizations are particularly suitable to produce high octane number branched paraffin mixtures of the gasoline range. As examples of commercial mixtures, straight-run type or light naphtha fractions from conventional refinery operations can be mentioned. Isomerization of alkylbenzenes include those of xylenes, cymenes, and other di- and poly-alkylbenzenes.

In carrying out isomerizations of isomerizible $C_4$ to $C_{20}$ hydrocarbons, contact between the catalyst and hydrocarbon charge is conducted at temperatures between about 0° and 200° C., preferably between about 20° and 100° C. at pressures between atmospheric and 25-atmospheres or more. The hydrocarbon is passed over the catalyst as a gas or liquid, with an hourly space velocity generally between about 0.5 and 5.0. The resulting product is withdrawn from the reactor, and is separated by any suitable means such as fractional distillation. Any unreacted starting material may be recycled. Superacidic isomerization catalysts generally also cause concurrent cleavage reactions (cracking).

The catalysts of the present invention are particularly suitable for catalytic cracking of hydrocarbons. The hydrocarbon charge may comprise normal paraffins or complex mixtures of paraffins, naphthenes, and aromatics, such as they occur in petroleum which is the feed normally used in commercial catalytic cracking units. Hydrocarbon cracking utilizing catalysts of the present invention can be conducted at temperatures ranging between 50° and 250° C. and pressures from atmospheric to 50 atmospheres or higher. Presence of hydrogen (hydrocracking) can be applied to further prolong catalyst life and thus cause more efficient cracking operations. It is of particular significance that the catalysts of the present invention, when based on non-reducible halides, such as tantalum and niobium pentafluoride, not including nobel metals, are very effective hydrocracking catalysts which are not effected by the presence of sulfur and other impurities which normally cause rapid deactivation of coventional cracking catalysts. In view of the need of increased utilization of "heavy" petroleums and lower grade crudes, the new catalysts and process of this invention is of considerable commercial significance.

Alkylations may also effectively carried out employing the catalysts of the present invention. Alkylation of alkylatable hydrocarbons such as paraffins or aromatics with olefins, alkyl halides, alcohols, and other alkylating agents can be effected in the presence of the catalyst at temperatures between about 0° to 200° C. and the pressure between about atmospheric and 30 atmosphere.

Catalysts of present invention are also effective to initiate cationic polymerization of polymerizible monomers, such as olefins. Even further, they are capable of causing oligocondensation of alkanes, including methane, ethane, propane, butanes, etc. or co-polymerization (condensation) of alkanes with alkenes, such as ethene, propene, butenes and the like.

The fluorinated graphite used to prepare the catalyst of this invention is well known and various methods for preparing such fluorinated graphite is also well known. See, for example, THE JOURNEY OF PHYSICAL CHEMISTRY, Vol. 69, No. 8, August 1965, pages 2772–2775, "Kinetics of the Reactions of Elemental Fluroine. IV. Fluorination of Graphite", and British Pat. No. 1,049,582, filed Jan. 31, 1964. The carbon fluoride or C/F ratio can easily be controlled and obtained by following or restricting the time of reaction, for example, and the exact C/F ratio determined by routine analysis.

The invention will be further described in connection with the following examples which are set forth for purposes of illustration only and are not to be construed as limiting the scope of the invention in any manner.

EXAMPLE 1

16 g of a fluorinated graphite having an F/C atomic ratio of 0.3 was dried under vacuum for 12 hours at 100° C. and transferred into a 100 cc reaction flask fitted with a reflux condenser, mechanical stirrer, and a nitrogen gas inlet. 6 g of $SbF_5$ dissolved in 50 ml dry 1,1,2-trichlorotrifluorethane was added into the flask under nitrogen and the mixture was stirred at 46° for six hours.

The solvent was then evacuated in vacuo and the mixture heated with occasional stirring in controlled temperature bath at 100° C. for a period of an additional 12 hours until no loss in weight or pressure increase was observed indicating complete bonding of the $SbF_5$.

10 g of this catalyst was charged into a fluid bed reactor and n-heptane (reagent grade 99+% purity) was passed continuously over the catalyst at 120° C. reaction temperature. Isomerization accompanied by cracking was observed. Conversion of n-heptane increased rapidly to about 40% and stayed constant for a period of about 6 hours. Cracking decreased relative to isomerization over this interval. Cracking can be further reduced by carrying out the reaction in the presence of hydrogen gas. Conversion subsequently slowly dropped to 25%. Results are summarized in Table I.

EXAMPLE 2

16 g of fluorographite having an F/C atomic ratio of 0.9 was dried under vacuum for 12 hours at 100° C., and then treated at 0° C. with 6 g of $NbF_5$ dissolved in HF. After two hours of stirring the temperature was raised to evaporate any excess HF to dryness. The mixture was heated and maintained at 100° C. for 6 hours until no loss of weight or pressure increase.

The catalyst was used in the isomerization of n-heptane in the same manner as described in Example 1. Results are summarized in Table I.

EXAMPLE 3

A catalyst composition was formed in the same manner as described in Example 2 except that $TaF_5$ was substituted for $NbF_5$.

The catalyst was used in the isomerization of n-heptane as described in Example 1. The results are summarized in Table 1.

TABLE I

| | Ex. I Fluoro-graphite-$SbF_5$ | Ex. II Fluoro-graphite-$NbF_5$ | Ex. III Fluoro-graphite-$TaF_5$ |
|---|---|---|---|
| Propane | 7.4 | 0.2 | 0.2 |
| Methylpropane | 14.1 | 11.8 | 11.2 |
| Butane | 3.2 | 1.8 | 0.2 |
| Methylbutane | 5.0 | 10.2 | 9.8 |
| Pentane | 0.9 | 1.4 | 1.5 |
| 2,2-Dimethylbutane | 0.2 | 1.3 | 0.8 |
| 2,3-Dimethylbutane | 0.5 | 3.1 | 3.4 |
| 3-Methylpentane | 0.1 | 1.1 | 1.1 |
| Hexane | 0.3 | 0.4 | 0.4 |
| 2,2-Dimethylpentane | | | |
| 2,4-Dimethylpentane | 0.2 | 0.8 | 0.8 |
| 2,2,3-Trimethylbutane | 0.1 | 0.2 | 0.1 |
| 3,3-Dimethylpentane | 0.1 | 0.1 | 0.3 |
| 2-Methylhexane | 1.0 | 1.1 | 1.2 |
| 2,3-Dimethylpentane | 0.3 | 0.4 | 0.3 |
| 3-Methylhexane | 0.7 | 0.8 | 0.9 |
| Heptane | 66.2 | 65.3 | 68.1 |

EXAMPLE 4

A catalyst comprising of $SbF_5$-$HSO_3F$ intercalated in fluorographite (F/C=0.3) was prepared by adding 6 g of $SbF_5$ to 20 g of fluorographite to a solution of 5.5 g of fluorosulfuric acid, diluted with 50 ml of trichlorotrifluoroethane (Freon 113). After stirring for 2 hours, the temperature was raised under a nitrogen atmoshere and then vacuum was applied to evaporate the Freon solvent of any volatile acid. Complete intercalation or bonding was indicated after constant weight was obtained. The catalyst, thus obtained, was used in the same manner described in Example 1 at a reaction temperature of 70° C. in the isomerization of n-hexane. Table II shows the results of a typical composition of the isomerization products.

TABLE II

| | | | |
|---|---|---|---|
| Isobutane | 2.4 | 2,2-DiMePentane | 1.4 |
| n-Butane | .3 | 2,4-DiMePentane | 2.3 |
| 2,2-DiMeProPropane | tr. | 2,2,3-TriMeButane | 1.1 |
| 2-MeButane | 8.54 | 3,3-DiMePentane | 1.1 |
| n-Pentane | 1.8 | 2-MeHexane | 3.4 |
| 2,2-DiMeButane | 18.6 | 2,3-DiMePentane | 1.2 |
| 2,3-DiMeButane | 3.2 | 3-MeHexane | 2.4 |
| 2-MePentane | 7.8 | 3-Eth.Pentane | .1 |
| 3,-MePentane | 3.6 | n-Heptane | tr. |
| n-Hexane | 34.4 | MeCycloHexane | tr. |
| | | Other Products | 6.3 |

EXAMPLE 5

A catalyst comprising of 0.5% platinum, and 20% of tantalum pentafluoride bonded or intercalated to fluorinated graphite with an F/C ratio of 0.3 was prepared by adding an aqueous solution of chloroplatinic acid containing 0.2 g of platinum to 25 g of the fluorinated graphite. The water was then removed in vacuum and the fluorographite intercalated in vacuum at 100°-120° for 8 hours under a stream of chlorine. Subsequently, the platinum was reduced with hydrogen. Tantalum pentafluoride was then introduced to the catalyst as in the previous Examples to give a catalyst containing about 20% $TaF_5$ and 0.5 g Pt.

A continuous flow reactor was charged with 6 g of the catalyst and dry n-hexane containing 1.5 mole percent dissolved hydrogen was passed through with a liquid hourly space velocity of 1 upflow through the catalyst, but maintained at 50° C. Table III shows the product composition after 4 hours operation.

TABLE III

| | | | |
|---|---|---|---|
| Propane | 0.4 | Methylcyclopentane | 0.2 |
| Butane | 0.3 | 2,2-DiMePentane | 1.2 |
| Isobutane | 8.2 | 2,4-DiMePentane | 0.3 |
| 2-MeButane | 14.3 | 2,2,3-TrimethylButane | 0.2 |
| n-Pentane | 1.1 | 3,3-DiMePentane | 2.1 |
| 2,2-DiMeButane | 5.6 | Cyclohexane | 0.8 |
| 2,3-DiMeButane | 12.7 | 2,-MeHexane | trace |
| 2-MePentane | trace | 2,3-DiMePentane | trace |
| 3-MePentane | 1.7 | 3-MeHexane | trace |
| n-Hexane | 51.5 | 3-EtPentane | 0.3 |

EXAMPLES 6, 7, 8, 9

A catalyst described in Example 4 was used for the alkylation of alkanes with olefins. Specific examples studied were the reactions of butane with butene-1, (Example 6), isobutane with ethylene (Example 7), n-butane with ethylene (Example 8), n-butane with propylene (Example 9). Results obtained are summarized in Table IV.

TABLE IV

| | Ex. 6 n-Butane-butene-1 | Ex. 7 Isobu-tane-ethylene | Ex. 8 n-Butane-ethylene | Ex. 9 n-Butane-propyl-ene |
|---|---|---|---|---|
| Butanes plus pentanes | 61 | 10 | 18 | 46 |
| Hexanes | 7 | 56 | 38 | 14 |
| 2,2-dimethylbutane | | 48 | 34 | |
| 2,3-dimethylbutane | | 11 | 16 | |
| 2-methylpentane | | 21 | 28 | |
| 3-methylpentane | | 12 | 16 | |
| n-hexane | | 8 | 6 | |

TABLE IV-continued

| | Ex. 6 n-Butane-butene-1 | Ex. 7 Isobutane-ethylene | Ex. 8 n-Butane-ethylene | Ex. 9 n-Butane-propylene |
|---|---|---|---|---|
| Heptanes | 5 | | | 29 |
| 2,2-dimethylpentane | | | | 1.5 |
| 2,4-dimethylpentane | | | | 26 |
| 2,2,3-trimethylbutane | | | | 10 |
| 3,3-dimethylpentane | | | | 1 |
| 2-methylhexane | | | | 26 |
| 2,3-dimethylpentane | | | | 16 |
| 3-methylhexane | | | | 19 |
| Octanes | 22 | | | 11 |
| Trimethylpentanes | 14 | | | |
| Dimethylhexanes | 54 | | | |
| Methylheptanes | 32 | | | |
| Heptanes plus higher | | 34 | 44 | |

EXAMPLE 10

Fluorographite bonded tantalum pentafluoride catalyst was prepared using a highly fluorinated graphite (F/C=0.9–1) treated with 6 g of tantalum fluoride dissolved in anhydrous HF (as described in the previous Examples). The temperature was subsequently raised to 100° C. for 6 hours in a nitrogen atmosphere to complete bonding. The catalyst was used in a continous flow reactor at 100° C. in the ethylation of benzene with ethylene utilizing a flow ratio of benzene to ethylene of 1.7 to 1.1 mmol per min. The results are summarized in Table V.

TABLE V

| Time, Hours | % Ethylbenzene | % Diethylbenzenes ortho | meta | para |
|---|---|---|---|---|
| 1 | 38.6 | 0.2 | 5.7 | 2.9 |
| 2 | 41.0 | 0.7 | 7.4 | 3.9 |
| 3 | 38.2 | 0.3 | 5.2 | 2.9 |
| 6 | 28.2 | 0.6 | 4.8 | 2.6 |

EXAMPLE 11

Transethylation of benzene with diethylbenzenes was carried out over a catalyst prepared from fluorographite (C/F 1.0–0.9) treated with 6 g of $TaF_5$, as described in the previous Examples. 7 g of the catalyst was charged into the continuous flow reactor and the reaction carried out at 130° with a feed ratio of 1 mml/min. benzene, 0.4 mml/m ethylbenzene.

TABLE VI

| Time, Hours | % Ethylbenzene | % Diethylbenzene ortho | meta | para | % Total Transethylation |
|---|---|---|---|---|---|
| 1 | 18.8 | <0.1 | 1.2 | 0.5 | 26.5 |
| 2 | 29.7 | 0.2 | 3.0 | 1.2 | 40.0 |
| 3 | 31.7 | <0.1 | 2.0 | 0.7 | 48.8 |
| 4 | 30.3 | <0.1 | 1.4 | 0.5 | 48.8 |
| 6 | 27.8 | <0.1 | 1.2 | 0.3 | 41.0 |

EXAMPLE 12

Transmethylation and isomerization of xylenes was carried out under conditions of Example 11, utilizing the same catalyst and as feed, p-xylene and benzene with a feed ratio of 1.1 mmol/min benzene to 0.44 mmol/min p-xylene. Data are summarized in Table VII. Of particular interest is the ability of the catalyst in also forming ethylbenzene in significant amounts.

TABLE VII

Transmethylation and Isomerization of Benzene with p-Xylene

| Time, hr. | % benzene | Composition of product mixture: toluene | ethylbenzene | p-xylene | in xylene |
|---|---|---|---|---|---|
| 1 | 81.7 | 3.8 | 6.9 | 6.4 | 1.2 |
| 2 | 80.5 | 2.4 | 10.9 | 5.3 | 0.8 |
| 3 | 74.6 | 2.2 | 17.6 | 4.8 | 0.8 |
| 4 | 69.5 | 3.1 | 25.6 | 5.6 | 1.2 |

EXAMPLE 13

Isomerization of xylenes can also be carried out in the liquid phase with dispersed fluorographite based catalysts, such as 20% fluorographitetantalum pentafluoride at 90° C. prepared in accordance with the previous Examples. Pure o-xylene under these conditions gave the following results

| time, hrs. | xylene composition % ortho | % meta | % para |
|---|---|---|---|
| 1 | 77.8 | 20.4 | 1.8 |
| 6 | 74.9 | 23.0 | 2.1 |
| whereas m-xylene isomerizes as shown | | | |
| 3 | 7.9 | 77.8 | 15.4 |

EXAMPLE 14

The oligo-condensation (polymerization) of alkanes was carried out in experiments using fluorographite-tantalum pentafluoride catalysts, prepared as described above, with 25% weight percent of the catalyst being stirred in a pressure vessel at an initial pressure of 35 atms. or less at 100° C. with the corresponding alkane. After 10 hours of reaction time, the following weight percent conversion to alkane polymers were observed (net weight <400)

| Alkane | Weight % of Conversion of Alkane Monomer to Polymer |
|---|---|
| Methane | 0.4 (mainly isobutane and isopentane) |
| Ethane | 2.1 $C_4$–$C_8$ mixture |
| Propane | 7.6 |
| n-Butane | 14.8 |

EXAMPLE 15

The copolymerization (co-condensation) of methane with ethylene (or propylene) was effected by reacting a 9:1 methane: ethylene (propylene) mixture over a tantalum and antimony pentafluoride-fluorographite, prepared as described above, catalyst at temperatures between 50° and 100° C. and a pressure of 1–20 atms. Conversion of products to liquid copolymer was observed incorporating up to 25% weight percent methane.

EXAMPLE 16

The polymerization of isobutylene to polyisobutylenes takes place with great ease when catalysts of this invention, such as 10% of the fluorographitetantalum pentafluoride catalyst, previously described, is dispersed into a suitable solvent, such as methylene chloride cooled to 50° to 30° C., and isobutylene is introduced into the mixture.

While the invention has been described in connection with preferred embodiments, it is not intended to limit the invention to the particular forms set forth, but on the contrary, it is intended to cover such alternatives, modifications, and equivalents as may be included within the spirit and scope of the invention as defined by the appended claims.

What is claimed is:

1. A process for effecting hydrocarbon conversion reactions which comprises contacting under hydrocarbon conversion conditions a hydrocarbon charge with a catalyst composition comprising a fluorinated graphite having a fluorine to carbon atomic ratios of from about 0..1 to 1 having bonded thereto from between about 5 to about 50 percent by weight of the total catalyst composition of at least one Lewis acid selected from halides of the elements of Group II-A, III-A, IV-B, V or VI-B of the pe.iodic Table.

2. A process for effecting hydrocarbon conversion reactions which comprises contacing under hydrocarbon conversion conditions a hydrocarbon charge with the catalyst composition of claim 1 wherein the fluorine to carbon atomic ratio is from about 0.1 to 0.6 and the Lewis acid compound selected from the halides of the elements of Group V to the Periodic Table.

3. A process for effecting a hydrocarbon conversion reaction which comprises contacting under hydrocarbon conversion conditions a hydrocarbon charge with the catalyst composition of claim 2 wherein the Lewis acid compound is antimony pentafluoride.

4. A process for effecting a hydrocarbon conversion reaction which comprises contacting under hydrocarbon conversion conditions a hydrocarbon charge with the catalyst composition of claim 2 wherein the Lewis acid compound is tantalum pentafluoride.

5. A process for effecting a hydrocarbon conversion reaction which comprises contacting under hydrocarbon conversion conditions a hydrocarbon charge with the catalyst composition of claim 2 wherein the Lewis acid compound is niobium pentafluoride.

6. A process for effecting hydrocarbon conversion reactions which comprises contacting under hydrocarbon conversion conditions a hydrocarbon charge with the catalyst composition of claim 1 wherein, in addition to the Lewis acid, a Bronsted acid is bonded to the fluorinated graphite in amounts of from about 1 to 50 percent by weight based on the weight of the Lewis acid.

7. A process for effecting hydrocarbon conversion reactions which comprises contacting under hydrocarbon conversion conditions a hydrocarbon charge with the catalyst composition of claim 6 wherein the Bronsted acid is selected from the group consisting of hydrogen fluoride, fluorosulphonic acid, and trifluoromethane sulphonic acid.

8. The process for effecting hydrocarbon conversion reactions which comprises contacting under hydrocarbon conversion conditions a hydrocarbon charge with the catalyst composition of claim 1 wherein, in addition to the Lewis acid, said composition contains from about 0. 1 to 5 percent by weight based on the Lewis acid of a metal selected from the metals of Groups IV-B and VIII of the Periodic Table.

9. The process for effecting hydrocarbon conversion reactions which comprises contacting under hydrocarbon conversion conditions the hydrocarbon charge with the catalyst composition of claim 8 wherein the metal is selected from the metals of Group VIII of the Periodic Table.

* * * * *

UNITED STATES PATENT AND TRADEMARK OFFICE

CERTIFICATE OF CORRECTION

PATENT NO. : 4,201,730

DATED : May 6, 1980

INVENTOR(S) : George A. Olah

It is certified that error appears in the above-identified patent and that said Letters Patent are hereby corrected as shown below:

Column 1, line 51, reads "ketoes" should read --ketones--

Column 4, line 27, reads "suport" should read --support--

Column 4, line 34 reads "terric" should read --ferric--

Column 5, line 15 reads "transformer" should read --transformation--

Column 6, line 24 reads "coventional" should read --conventional--

Column 6, line 29 reads "may also" should read --may be also--

Column 6, line 47 reads "JOURNEY" should read --JOURNAL--

Column 11, line 12 reads "ratios" should read --ratio--

Signed and Sealed this

*Twenty-sixth* Day of *August 1980*

[SEAL]

*Attest:*

SIDNEY A. DIAMOND

*Attesting Officer*

*Commissioner of Patents and Trademarks*